United States Patent
Srinath et al.

(10) Patent No.: US 8,115,013 B2
(45) Date of Patent: Feb. 14, 2012

(54) PROCESS FOR THE PREPARATION OF AMORPHOUS FLUVASTATIN SODIUM

(75) Inventors: Sumithra Srinath, Karnataka (IN); Tom Thomas Puthiaprampil, Karnataka (IN); Ravindra Chandrapa, Karnataka (IN); Sambasivam Ganesh, Karnataka (IN)

(73) Assignee: Biocon Limited, Bangalore, Karnataka (IN)

( * ) Notice: Subject to any disclaimer, the term of this patent is extended or adjusted under 35 U.S.C. 154(b) by 416 days.

(21) Appl. No.: 11/576,714

(22) PCT Filed: Oct. 5, 2004

(86) PCT No.: PCT/IN2004/000310
§ 371 (c)(1), (2), (4) Date: Jan. 23, 2008

(87) PCT Pub. No.: WO2006/038219
PCT Pub. Date: Apr. 13, 2006

(65) Prior Publication Data
US 2008/0262245 A1    Oct. 23, 2008

(51) Int. Cl.
*C07D 209/04* (2006.01)

(52) U.S. Cl. ......................................................... 548/491

(58) Field of Classification Search .................. 548/491
See application file for complete search history.

(56) References Cited

U.S. PATENT DOCUMENTS

| 4,739,073 A | * | 4/1988 | Kathawala | ................... 548/406 |
| 7,414,140 B2 | * | 8/2008 | Lifshitz-Liron et al. | ....... 548/494 |

FOREIGN PATENT DOCUMENTS

| WO | WO 97/49681 | * | 6/1997 |
| WO | 02/36563 |   | 5/2002 |
| WO | WO 2004/096765 | * | 4/2004 |

OTHER PUBLICATIONS

Tempkin et al. (Tetrahedron (1997), vol. 53, No. 31; p. 10659-10670.*
Tempkin et al., Asymmetric Synthesis of 3,5-Dihydroxy-6(E)-heptenoate-containnig HMG-CoA Reductase Inhibitors, Tetrahedron, 1997, vol. 53, No. 31, pp. 10659-10670.

* cited by examiner

*Primary Examiner* — Yong Chu
*Assistant Examiner* — Valerie Rodriguez-Garcia
(74) *Attorney, Agent, or Firm* — Allen, Dyer, Doppelt, Milbrath & Gilchrist, P.A.

(57) ABSTRACT

The present invention relates to a novel process for the preparation of the HMG-CoA reductase inhibitor, fluvastatin, more specifically to a process for the preparation of amorphous form of fluvastatin sodium.

4 Claims, 2 Drawing Sheets

PROCESS FOR THE PREPARATION OF AMORPHOUS FLUVASTATIN SODIUM

FIELD OF THE INVENTION

The instant invention relates to a novel process for the preparation of the HMG-CoA reductase inhibitor, fluvastatin, more specifically to a process for the preparation of amorphous fluvastatin sodium.

BACKGROUND OF THE INVENTION

Fluvastatin, of which the full chemical name is R*,S*-(E)-(.+-.)-7-[3-(4-fluorophenyl)-1-(1-methyl-ethyl)-1H-indol-2-yl]-3,5-dihydroxy-6-heptenoic acid, as well as its sodium salt, are disclosed in EP-A-0 114 027. Fluvastatin is an inhibitor of 3-hydroxy-3-methyl-glutaryl coenzyme A (HMG-CoA) reductase, which is a key enzyme in the regulation of cholesterol biosynthesis. Fluvastatin can be used pharmaceutically particularly as a hypercholesterolemic, hyperlipoproteinemic and antiatherosclerotic agent.

The present invention relates to a novel process for the preparation fluvastatin form A. Polymorphism is the existence of more than one crystal structure for a compound. Since properties can and do vary with crystal structure, polymorphism can influence many important properties of pharmaceuticals: bioavailability, dissolution rate, compressibility, solubility, stability, filtering and drying characteristics etc. Different combination of experimental techniques (microscopy, variable temperature X-ray structure determination, spectroscopic and calorimetric methods) are used to discover, prepare, characterize, and study polymorphs of compounds of pharamceutical importance.

Many pharmaceutical materials exhibit polymorphism during heating and this refers to the generation of thermodynamically unstable melting forms. These polymorphic forms can be produced due to the given thermal history of the material. Different polymorphic forms can have differing solubilities and this can have a potentially major effect on the bioavailability of the drug when ingested. One polymorphic form may dissolve rapidly while another is very slow to dissolve. It is essential to screen pharmaceuticals for polymorphism for process optimization and for quality assurance purposes.

Fluvastatin sodium is specifically claimed as a substance in U.S. Pat. No. 5,354,772.

Polymorphic forms of Fluvastatin sodium are claimed in various patent applications viz. WO 97/49681, WO 02/36563 and WO 03/013512.

WO 97/49681 (equivalent U.S. Pat. No. 6,124,340 and EP 0 907 639) claims fluvastatin sodium crystalline form B. The PCT publication has compared properties of form B with form A. In accordance to WO 97/49681, the form A could be obtained by lyophilization process disclosed in U.S. Pat. No. 4,739,073. Several of these prior art process often result in a mixture of amorphous form and different crystalline form.

The present invention provides a robust process for the preparation of fluvastatin sodium in a amorphous form. The amorphous form of fluvastatin sodium thus prepared is substantially free from the anti-isomer.

SUMMARY OF THE INVENTION

The invention relates to a novel process for the preparation of amorphous form of sodium fluvastatin.

BRIEF DESCRIPTION OF THE DRAWINGS

Some of the features, advantages, and benefits of the present invention having been stated, others will become apparent as the description proceeds when taken in conjunction with the accompanying drawings, presented solely for exemplary purposes and not with intent to limit the invention thereto, and in which.

DETAILED DESCRIPTION OF THE INVENTION

Figure 1:
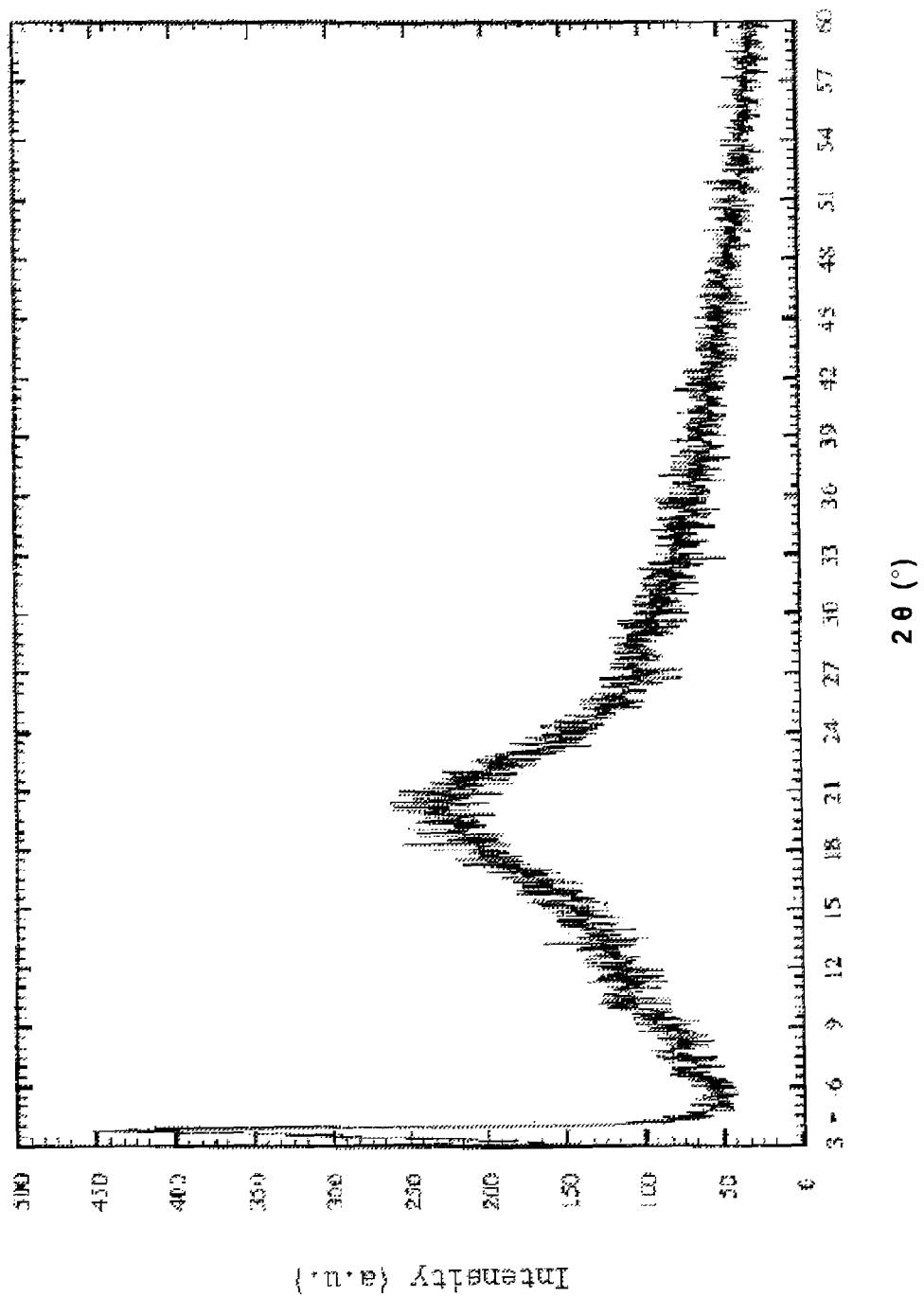
FIG. 1 shows an X-ray diffraction pattern for the compoud of Example 1, according to an embodiment of the present invention.
Figure 2:
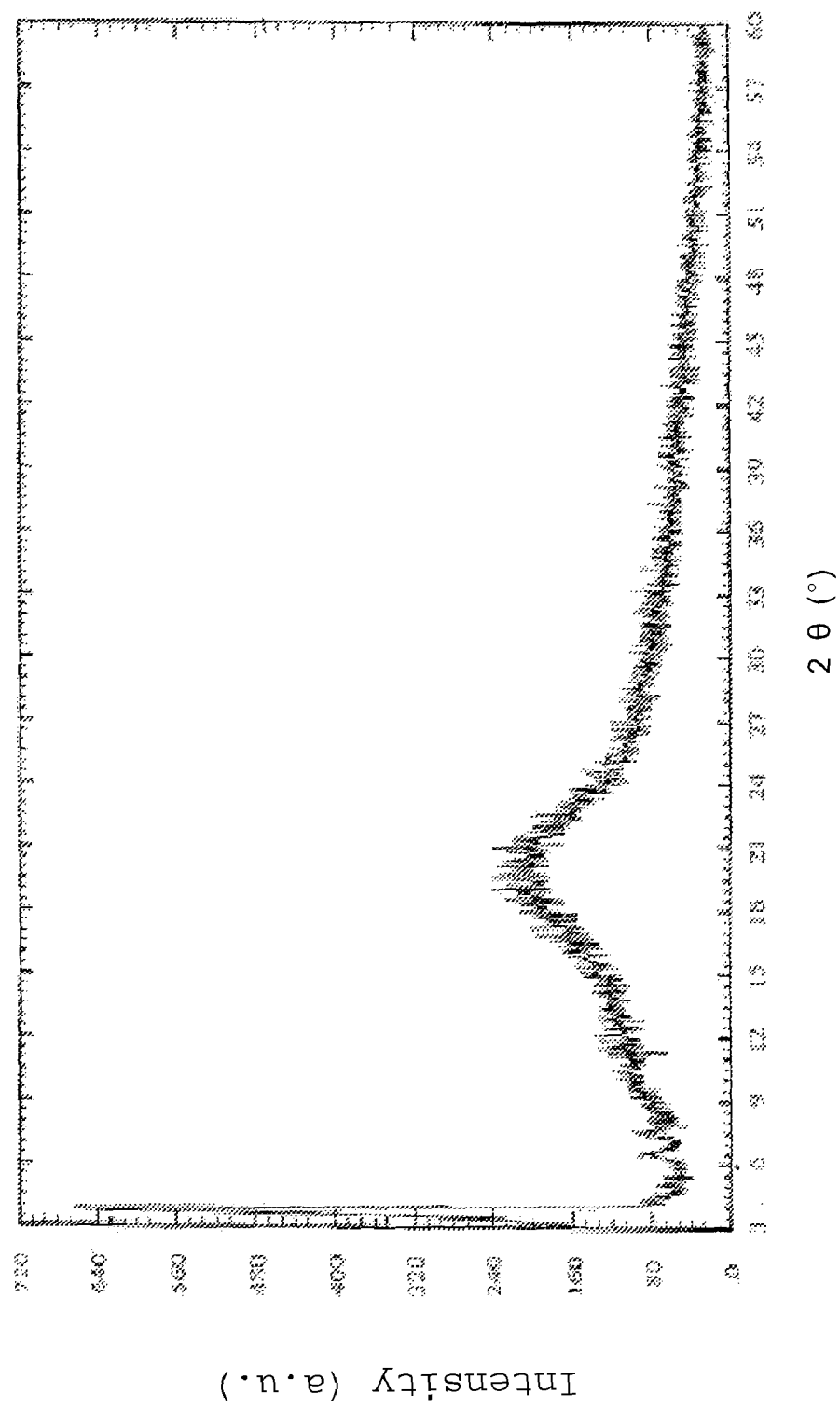
FIG. 2 provides an X-ray diffraction pattern for the compound of Example 2, according to an embodiment of the present invention.

The present invention relates to a novel process for the preparation of the HMG-CoA reductase inhibitor, fluvastatin, more specifically to a process for the preparation of amorphous form of fluvastatin sodium.

The instant invention discloses a process for the preparation of amorphous form of fluvastatin sodium comprising of:
(a) dissolving the sodium fluvastatin in methanol followed by stirring,
(b) concentrating the methanol extract to get a residue,
(c) isolating the residue to get amorphous form of fluvastatin sodium.

The process further comprising of
(d) subjecting the isolated amorphous form of fluvastatin sodium to drying.

The process where the amorphous fluvastatin sodium in step (c) is isolated by filtration.

The process where the amorphous form of fluvastatin sodium is vacuum dried.

The instant invention has following advantages over prior art:
1. The process is robust resulting in amorphous form only.
2. The product prepared by the process is chemically stable.
3. The process is simple and economic
4. The process is environmentally friendly.

The present invention is further illustrated by the following non-limiting examples.

EXAMPLES

Example 1

To a solution of t-butyl (E)-3,5-dihydroxy-7-[3'-(4"-fluorophenyl)-1'-methylethyl-indol-2'-yl]hept-6-enoate (1.0 Kg) in methanol (10 L), a solution of sodium hydroxide (90 g) in methanol (1.0 L) was added stirred for 2 h. The reaction mixture was concentrated. The residue was dissolved in methanol (5.0 L) and filtered over celite bed. The clear filtrate concentrated to syrup. Methanol (3.0 L) was added to the residue and stirred for 30 minutes. The mixture was concentrated and residue was dried in vacuum drier. The XRD pattern of the product showed that the product corresponds to amorphous fluvastatin sodium. Yield: 480 g.

Example 2

Fluvastatin sodium form A (1.0 Kg) was dissolved in methanol (10 L) and filtered over celite bed. The clear filtrate concentrated to syrup. Methanol (5.0 L) was added to the residue and stirred for 30 minutes. The mixture was concentrated and residue was dried in vacuum drier. The XRD pattern of the product showed that the product corresponds to amorphous fluvastatin sodium. Yield: 980 g.

We claim:

1. A process for the preparation of an amorphous form of fluvastatin sodium, the process comprising:
    preparing a solution by dissolving the sodium fluvastatin in methanol;
    filtering the solution through a bed of diatomaceous earth to obtain a filtrate; and
    evaporating the filtrate to obtain a residue of amorphous fluvastatin sodium.

2. The process of claim 1, further comprising drying the amorphous residue of fluvastatin sodium.

3. The process of claim 1, wherein evaporating further comprises drying under vacuum.

4. The process of claim 1, wherein filtering further comprises Celite brand of diatomaceous earth.

* * * * *